(12) United States Patent
Batzinger et al.

(10) Patent No.: US 6,789,427 B2
(45) Date of Patent: Sep. 14, 2004

(54) PHASED ARRAY ULTRASONIC INSPECTION METHOD FOR INDUSTRIAL APPLICATIONS

(75) Inventors: Thomas James Batzinger, Burnt Hills, NY (US); Wei Li, Niskayuna, NY (US); Robert Snee Gilmore, Burnt Hills, NY (US); Edward James Nieters, Burnt Hills, NY (US); William Thomas Hatfield, Schenectady, NY (US); Richard Eugene Klaassen, West Chester, OH (US); James Norman Barshinger, Aaronsburg, PA (US); Bruno Hans Haider, Ballston Lake, NY (US); Carl Lawrence Chalek, Glenville, NY (US); Robert John McElligott, Loveland, OH (US); David Charles Franklin, Cincinnati, OH (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/244,637

(22) Filed: Sep. 16, 2002

(65) Prior Publication Data

US 2004/0050166 A1 Mar. 18, 2004

(51) Int. Cl.$^7$ .................................................. G01N 9/24

(52) U.S. Cl. ............................ 73/614; 73/618; 73/625

(58) Field of Search ........................... 73/614, 618, 622, 73/625, 626, 628, 861.23, 861.25; 600/447, 441, 443, 444, 445

(56) References Cited

U.S. PATENT DOCUMENTS

| 4,180,790 A | | 12/1979 | Thomas ........................ 73/626 |
| 4,180,791 A | | 12/1979 | Tiemann ....................... 73/626 |
| 4,438,652 A | * | 3/1984 | Saito ........................ 73/861.25 |
| 4,471,785 A | | 9/1984 | Wilson et al. ............... 600/447 |
| 4,523,468 A | * | 6/1985 | Derkacs et al. ................ 73/598 |
| 4,660,419 A | * | 4/1987 | Derkacs et al. ................ 73/622 |
| 4,718,277 A | * | 1/1988 | Glascock ....................... 73/622 |
| 5,014,712 A | | 5/1991 | O'Donnell .................... 73/625 |
| 5,111,695 A | | 5/1992 | Engeler et al. ................ 73/626 |
| 5,230,340 A | | 7/1993 | Rhyne ......................... 600/447 |
| 5,235,982 A | | 8/1993 | O'Donnell ................... 600/443 |
| 5,329,930 A | | 7/1994 | Thomas, III et al. ........ 600/447 |
| 5,345,939 A | | 9/1994 | Engeler et al. ............... 73/602 |
| 5,406,949 A | * | 4/1995 | Yao et al. .................... 600/457 |
| 5,431,054 A | * | 7/1995 | Reeves et al. ................ 73/612 |
| 5,463,905 A | * | 11/1995 | Baird ........................ 73/861.25 |
| 5,487,306 A | | 1/1996 | Fortes ......................... 73/597 |
| 5,490,512 A | | 2/1996 | Kwon et al. ................. 600/447 |
| 5,497,662 A | * | 3/1996 | Dykes .......................... 73/634 |

(List continued on next page.)

FOREIGN PATENT DOCUMENTS

| EP | 0818678 | 1/1998 |
| EP | 1109017 | 6/2001 |
| WO | 0008459 | 2/2000 |

*Primary Examiner*—Hezron Williams
*Assistant Examiner*—Jacques M. Saint-Surin
(74) *Attorney, Agent, or Firm*—Penny A. Clarke; Patrick K. Patnode (57) ABSTRACT

A method for inspecting a component includes exciting a number of transducers forming an array to produce an ultrasonic transmission beam (beam) focused into the component. The array and the component are separated by a standoff. A number of echo signals are generated using the transducers, and the echo signals are processed in a number of channels. The processing includes both dynamical focus and providing a dynamic aperture on receive, both of which compensate for refraction of the beam at the component/standoff interface. A single-turn inspection method includes: (a) positioning the array facing the component, (b) exciting the transducers, (c) generating a number of echo signals, (d) changing the relative angular orientation of the array and the component around an axis and repeating steps (b) and (c), and (e) processing the echo signals to form at least one processed echo signal.

12 Claims, 7 Drawing Sheets

U.S. PATENT DOCUMENTS

| | | | | |
|---|---|---|---|---|
| 5,563,346 A | | 10/1996 | Bartelt et al. | 600/459 |
| 5,568,813 A | | 10/1996 | Deitrich et al. | 600/447 |
| 5,606,972 A | * | 3/1997 | Routh | 600/455 |
| 5,740,806 A | | 4/1998 | Miller | 73/626 |
| 5,817,023 A | | 10/1998 | Daft | 600/447 |
| 5,853,367 A | | 12/1998 | Chalek et al. | 600/437 |
| 5,891,038 A | | 4/1999 | Seyed-Bolorforosh et al. | 600/447 |
| 5,897,501 A | | 4/1999 | Wildes et al. | 600/447 |
| 5,902,241 A | | 5/1999 | Seyed-Bolorforosh et al. | 600/443 |
| 5,936,162 A | | 8/1999 | Lingenberg et al. | 73/643 |
| 5,951,479 A | | 9/1999 | Holm et al. | 600/443 |
| 6,016,285 A | * | 1/2000 | Wright et al. | 367/11 |
| 6,019,001 A | | 2/2000 | Schreiner et al. | 73/640 |
| 6,035,696 A | * | 3/2000 | Kiefer et al. | 73/1.82 |
| 6,048,315 A | | 4/2000 | Chiao et al. | 600/447 |
| 6,056,693 A | | 5/2000 | Haider | 600/443 |
| 6,183,419 B1 | | 2/2001 | Wildes | 600/447 |
| 6,210,332 B1 | | 4/2001 | Chiao et al. | 600/443 |
| 6,296,612 B1 | | 10/2001 | Mo et al. | 600/455 |
| 6,436,044 B1 | | 8/2002 | Wang | 600/437 |
| 6,568,271 B2 | * | 5/2003 | Shah et al. | 73/599 |
| 6,663,568 B1 | * | 12/2003 | Gill | 600/456 |

* cited by examiner

PHASED ARRAY ULTRASONIC INSPECTION METHOD FOR INDUSTRIAL APPLICATIONS

BACKGROUND OF THE INVENTION

The invention relates generally to ultrasonic imaging methods for industrial applications and, more particularly, to improved ultrasonic imaging methods for the detection of defects found in components and structures (collectively termed "components") found in industrial settings using advanced phased array ultrasound systems.

Both the use of lighter components in industrial applications and the use of industrial components over longer engineering design lives have increased the demand for enhanced nondestructive inspection techniques designed for industrial settings. To meet current demands, it is necessary to detect smaller defects with greater productivity. Medical imaging tools, such as the GE LOGIQ 9 and the GE LOGIQ Book, include many features that would be desirable for industrial applications.

Conventional ultrasonic inspection systems for industrial applications employ either probes with fixed focus lenses or limited capability phased array imaging techniques. Limitations include performing inspections within the focal depth of field, in the case of the fixed focus lens systems, or within the limits of the phased array system to produce a focused beam. Generally, conventional ultrasonic systems for industrial applications use either a single probe, in pulse echo mode, or a pair of probes, in either a through transmission or pitch and catch mode. These probes can be either unfocused or focused using an attached lens. Industrial inspections requiring high sensitivity over a large depth range are typically accomplished using multiple scans with appropriately focused probes. Such inspections are time consuming due to the multiple scans required. High-sensitivity, large depth range inspections are also performed using a multi-zone approach, in which multi-channel acquisition systems are used to monitor data from multiple probes simultaneously, with each probe monitoring a separate depth within the test component. Conventional ultrasonic inspection systems for industrial applications are typically limited to a single angle beam interrogation of the test component. The angled ultrasonic beam is produced either by affixing the probe to a wedge of material at an angle relative to the test component or by immersion of the probe in a material with a material velocity, which is sufficiently different from that of the test component to cause refraction of the beam.

Conventional phased array imaging ultrasound systems for industrial inspections typically are limited to beamforming, with the more advanced of these systems providing dynamic depth focus but incapable of performing dynamic aperture sizing. Dynamic aperture sizing is desirable to control the beam properties.

It would therefore be desirable to provide an inspection method for industrial applications that provides both dynamic focus and dynamic aperture sizing. It would further be desirable for the method to compensate for refraction at an interface between a test component and a standoff, for example a water standoff. It would also be desirable to provide an inspection method for industrial applications that compensates for the steering of the ultrasonic transmission beam due to refraction at a test component/standoff interface. In addition, it would be desirable to correct for surface geometry effects caused by a curved test component/standoff interface. To increase productivity, it would also be desirable to provide a single-turn inspection method, so that industrial components can be inspected without time-consuming movement of a probe. It would also be desirable to provide a method to inspect the quality of the product flow through pipes that employs ultrasonic inspection techniques. To decrease inspection time, it would be desirable to employ full-array insonification. Also, for industrial applications, it would be desirable to introduce synchronization of images with the corresponding probe position to advanced ultrasound imaging systems typically employed for medical applications.

BRIEF DESCRIPTION

Briefly, in accordance with one embodiment of the present invention, a method of inspecting a component is provided. The inspection method includes exciting a number of transducers forming an array to produce an ultrasonic transmission beam focused into the component along a selected ray path from the array. The array is separated from the component by a standoff with a material velocity $v_w$. The inspection method further includes generating a number of echo signals using the transducers as receive elements and processing the echo signals in a number of channels. The processing includes dynamically focusing the echo signals along the selected ray path on at least one focal point P in the component. The dynamic focusing comprises adjusting a delay profile to compensate for refraction of the ultrasonic transmission beam at an interface between the component and the standoff and applying the delay profile to the echo signals in the respective channels to generate a number of delayed echo signals. The processing further includes adjusting the number of active receive elements as a function of a range $R_g$, to provide a dynamic aperture on receive. The adjustment of the number of receive elements comprises compensating for refraction of the ultrasonic transmission beam at the interface between the component and the standoff. The processing also includes summing the delayed echo signals from the active receive elements to generate a focused echo signal.

Another method embodiment for inspecting a component includes applying a separate excitation pulse to each transducer in the array, to produce an ultrasonic transmission beam focused into the component along a selected ray path. As above, the array is separated from the component by a standoff with a material velocity $v_w$. The inspection method further includes steering the ultrasonic transmission beam along the selected ray path at an angle θ relative to a surface normal. The steering comprises adjusting a transmit delay profile, to compensate for refraction of the ultrasonic transmission beam at the interface between the component and the standoff, and modulating the excitation pulses with the transmit delay profile. The inspection method further includes generating a number of echo signals using the transducers as receive elements and processing the echo signals in a number of channels using a delay profile that comprises a number of receive delays, each receive delay comprising a static receive steering term. The echo signal processing includes adjusting each of the static receive steering terms to compensate for refraction of the ultrasonic transmission beam at the component/standoff interface, applying the delay profile to the echo signals in the respective channels to generate a number of delayed echo signals, and summing the delayed echo signals from the receive elements to generate a steered echo signal.

A single-turn method embodiment for inspecting a component having an inspection surface is also provided. The single-turn inspection method includes (a) positioning an array of transducers facing the inspection surface of the component, (b) exciting the transducers to produce an ultrasonic transmission beam focused into the component along a selected ray path from the array, (c) generating a number of echo signals using the transducers as receive elements, (d) changing the relative angular orientation of the array and the component around an axis and repeating steps (b) and (c), and (e) processing the echo signals in a number of channels to form at least one processed echo signal.

A method embodiment for inspecting product flow through a pipe is also provided. This inspection method includes exciting a number of transducers forming an array to transmit ultrasonic energy into the pipe, generating a number of receive signals from the reflected ultrasonic energy, and processing the receive signals in a number of channels. The processing comprises comparing the receive signals to a frequency reference to determine a number of frequency shifts imparted to the reflected ultrasonic energy.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

A. Dynamic Aperture and Dynamic Focus

Figure 1:
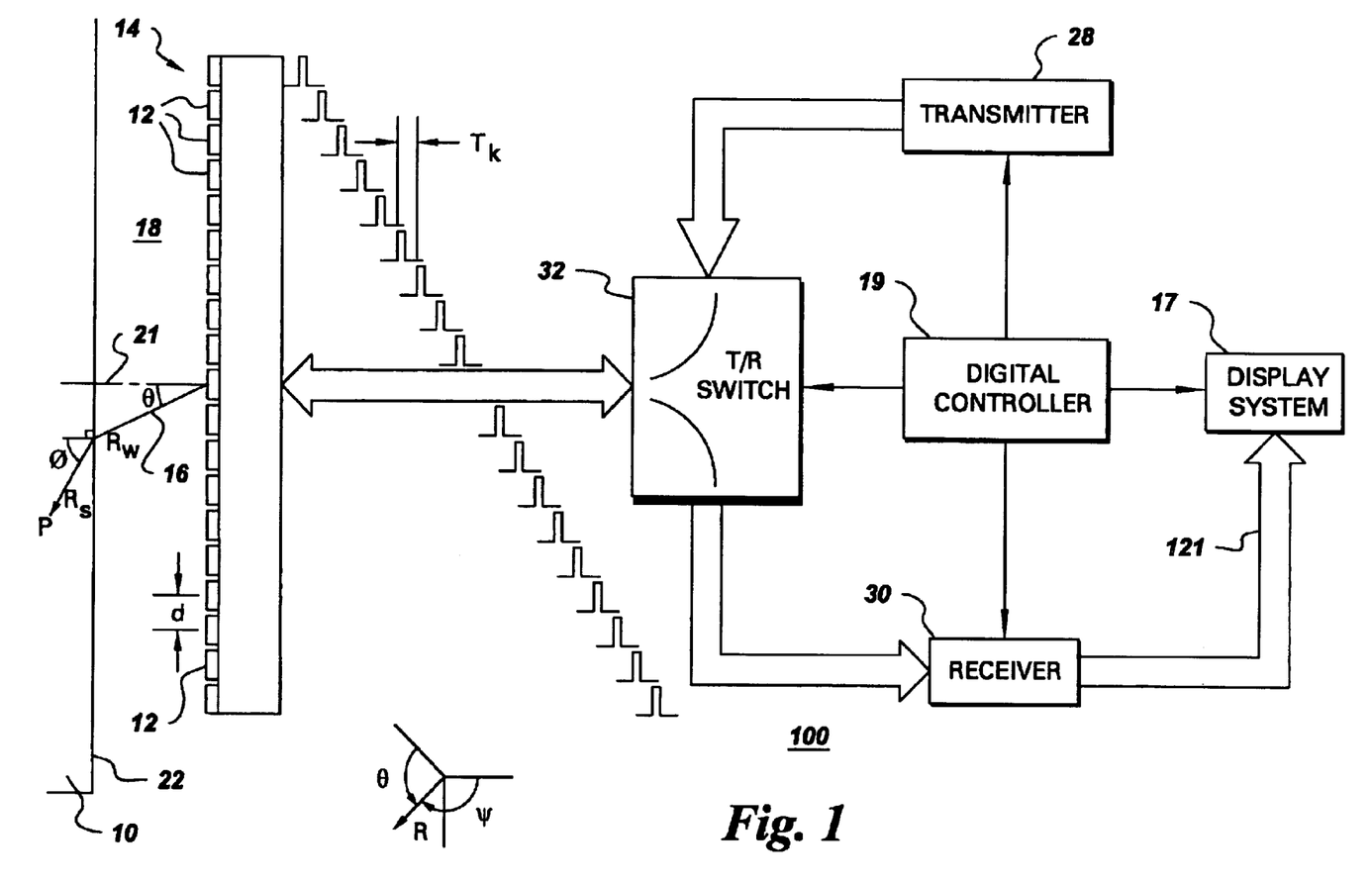
FIG. 1 is a block diagram of an ultrasonic imaging system.
Figure 2:
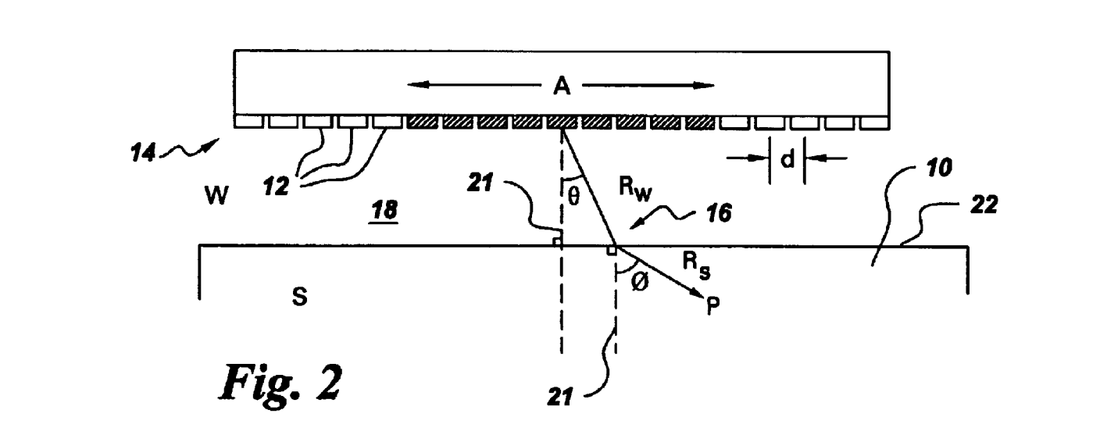
FIG. 2 shows an array and a component separated by a standoff, the component and standoff having different material velocities $v_s$, and $v_w$, respectively.

A method of inspecting a component 10 is described with reference to FIGS. 1 and 2. The method includes exciting a number of transducers 12 forming an array 14 to produce an ultrasonic transmission beam focused into the component 10 along a selected ray path 16 from the array, as shown in FIG. 1, which illustrates an ultrasonic imaging system 100 in block diagram form. Each of the transducers 12 is excited, for example, by a pulse produced by a transmitter 28. As shown in FIG. 2, the array 10 is separated from the component 10 by a standoff 18 with a material velocity $c_w$. Exemplary standoffs 18 include water, other fluids such as oils and glycerine, and a machined wedge (shoe). Examples of shoes (not shown) are solid structures machined to mate with the geometry of the transducer surface, on one side, and the component geometry on the other side. Shoes are often formed of plexiglass or Lucite. The method further includes generating a number of echo signals using the transducers 12 as receive elements 12, and processing the echo signals in a number of channels 20. For example, the ultrasonic energy reflected back to the array 14 is converted to an electrical signal (echo signal) by each of the transducers 12 and applied separately to a receiver 30 through a set of switches 32. For the exemplary system shown in FIG. 1, the transmitter 28, receiver 30, and switches 32 are controlled by a digital controller 19 responsive to commands input by an operator.

The processing includes dynamically focusing the echo signals along the selected ray path 16 on at least one focal point P in the component 10. The dynamic focusing includes adjusting a delay profile comprising a number of receive delays to compensate for refraction of the ultrasonic transmission beam at the interface 22 between the component 10 and the standoff 18. Exemplary receive delays include time and/or phase delays, which are indicated in FIG. 1 by ($T_k$). In the case of a linear array 14, each of the receive delays includes a beam focusing time delay that changes during reception of the echo to provide dynamic focusing of the received ultrasonic energy at the range from which the echo signal emanates. As explained in commonly assigned U.S. Pat. No. 5,235,982, O'Donnell, entitled "Dynamic transmit focusing of a steered ultrasonic beam," which is incorporated herein by reference, the delays may ordinarily be expressed as:

$$T_k = (k-(N-1)/2)^2 d^2 \cos^2 \theta / 2Rv,$$

where R is the range of the focal point P from the center of the array 14, v is the material velocity of the component 10, and θ is the angle of incidence for the beam 16 relative to a surface normal 21. However, this expression does not compensate for refraction at a component/standoff interface 22. An exemplary adjustment of this expression to compensate for the refraction across interface 22 is:

$$T_k = [k-(N-1)/2]^2 d^2 \cos^2 \theta / [2(R_w v_w + R_s v_s)],$$

where $R_w$, is the length of the beam extending along the central beam axis 16 in the standoff 18, $v_w$ is the material velocity in the standoff 18, $R_s$ is the length of the beam extending along the central beam axis 16 in the component 10, and $v_s$ is the material velocity in the component 10. The delay profile is applied to the echo signals in the respective channels 20 to generate a number of delayed echo signals. For example, receiver 30 samples the echo signals at a succession of ranges $R_s$ ($R_w$ is constant for a given angle θ) and provides the proper receive delays to dynamically focus at points P along the sampled beam. Thus, each emission of an ultrasonic pulse results in the acquisition of a series of echo signal samples that represent the amount of reflected sound from a corresponding series of points P located along the ultrasonic receive beam.

To provide a dynamic aperture 24 on receive, the processing further includes adjusting the number of active receive elements as a function of a range $R_s$. ($R_w$ is constant for a given incident angle θ.) As used here, the phrase "active receive element" 12 indicates a transducer from which the echo receive signal is included in the overall focused echo signal. Exemplary active receive elements are indicated in FIG. 2 by shading. In contrast, the echo signals from inactive receive elements 12 are neglected when calculating the focused echo signal. The adjustment of the number of receive elements 12 includes compensating for refraction of the ultrasonic transmission beam at the interface 22 between the component 10 and the standoff 18. For example, for an ultrasonic beam 16 incident on a component with no significant change in material velocity at the surface of the component, to maintain a constant focal number F, the aperture width A is adjusted according to the formula F=R/A. So for this conventional example, as the range R increases, A must also be increased to maintain a constant focal number F. In other words, the delayed echo signals of more active receive elements 12 contribute to the focused echo signal. As noted above, the ultrasonic transmission beam 16 is refracted at the interface 22 of the component 10 and the standoff 18, due to the mismatch in material velocities $v_w$ and $v_s$. To compensate for the refraction, adjustment of the aperture width A is performed according to the expression: $F=[R_w+Rs(v_s/v_w)]/A$.

In addition to the dynamic focusing and dynamic aperture sizing described above, the processing further includes summing the delayed echo signals from all of the active receive elements to generate a focused echo signal. For example, the delayed echo signals are summed in receiver 30 to form the focused echo signal, which may be employed, for example, to produce a pixel or a line in an image on a display 17.

Although the provision of dynamic aperturing and dynamic focusing has been described with respect to a component 10 and an array 14 separated by a standoff 18 with a material velocity mismatch, this combination is also applicable to contact ultrasonic inspection of a component 10, for example, for industrial inspection applications. By "contact," it is meant that the array 14 is placed in direct contact with the component 10. (Not shown in FIGS. 1 and 2.) However, where there is no standoff 18, there is no material velocity mismatch at the surface 22 of the component 10, and hence no refraction at the surface 22 of the component 10. Consequently, the dynamic aperturing and focusing are not corrected to compensate for refraction at the surface 22 of the component for ultrasonic inspection of a component 10 without a standoff 18. Dynamic aperture sizing and focusing in the absence of a standoff 18 are described, for example, in commonly assigned U.S. Pat. No. 4,180,790, Charles E. Thomas, entitled "Dynamic Array Aperture and Focus Control for Ultrasonic Imaging Systems," which is incorporated by reference herein.

Beneficially, the use of a dynamic aperture coupled with dynamic focusing enables controlling desired focal properties over the entire depth of inspection.

It is desirable for the array 14 to contain a large number of transducers 12, for example 128 or 1024, to provide a large inspection area. To enable the use of a large number of transducers without a corresponding increase in the number of channels 20 and to reduce the number of switches 32 needed, the transducers 12 may be multiplexed, for example as described in commonly assigned U.S. Pat. No. 5,329,930, Thomas et al., entitled "Phased Array Sector Scanner with Multiplexed Acoustic Transducer Elements," which is incorporated by reference herein. Beneficially, the use of 128 transducers 12 independently or 1024 transducers 12 via multiplexing facilitates improved productivity and inspection flexibility relative to conventional industrial ultrasonic inspection methods.

It is desirable to direct or steer the ultrasonic beam to move the beam through a set of angles θ to scan the component 10. According to a more particular embodiment, a separate excitation signal pulse is applied to each of the transducers, to drive each of the transducers 12 with separate voltages (apodizing). For this embodiment, which is illustrated in FIG. 2, the inspection method further includes steering the ultrasonic transmission beam along the selected ray path 16 at an angle θ relative to the surface normal 21. The steering includes adjusting a transmit delay profile to compensate for refraction of the ultrasonic transmission beam at the interface 22. The transmit delay profile comprises a set of transmit delays, and each transmit delay includes a static steering term. Exemplary transmit delays include time and/or phase delays, which are also indicated in FIG. 1 by ($T_k$). The steering further includes modulating the excitation signal pulses with the transmit delay profile. For example, transmitter 28 imparts a transmit delay to each of the signal pulses applied to the successive transducer elements 12. If the transmit delay is zero ($T_k$=0), all of the transducer elements 12 are energized simultaneously, and the resulting ultrasonic beam is directed normal to the interface 22 between the standoff 18 and the component 10. To steer the ultrasonic beam, the transmit delay $T_k$ that is added to the respective kth signal pulse from one end of the array 14 (k=1) to the other end (k=N) can be expressed as:

$$T_k(\theta)=(d/v_w)\sin\theta(k-1),$$

where d is the distance between transducer elements 12, as shown in FIG. 1. This transmit delay profile ($T_k$) compensates for the refraction of the steered ultrasonic beam at the interface 22.

In addition to steering the ultrasonic beam on transmit, the inspection method also includes forming a steered focused echo signal by application of the delay profile to the echo signals in the respective channels to generate the delayed echo signals (steering on receive). For this steering embodiment, the delay profile includes a set of receive delays, and each receive delay comprises a static receive steering term. Each of the static receive steering terms is adjusted to compensate for refraction at the interface. Each of the static receive steering terms for reception is the same delay $T_k(\theta)$ as the transmit delay explained above. Although only one angle (θ) is indicated, those skilled in the art will recognize that the ultrasonic beam may also be steered along multiple angles (θ, ψ) with respect to a common axis 21. This embodiment encompasses both single-angle (θ) and multi-angle (θ, ψ) steering.

In order to scan the component 10 at various depths $R_s$, multiple transmits are used. For this particular embodiment of the inspection method, a separate signal pulse is applied to each of the transducers 12 at each of a number of successive excitation time intervals $t_i$, and the generation of the echo signals is performed for each of the successive excitation time intervals $t_i$. For example, at a first time interval $t_1$, each of the transducers 12 is separately driven, and a first set of echo signals is generated. At a second time interval $t_2$, each of the transducers 12 is separately driven, and a second set of echo signals is generated, and so on. For this embodiment, the echo signals are dynamically focused along the selected ray path 16 at a number of focal points $P_i$, at various ranges $R_i$ during each successive i-th one of the excitation time intervals $t_i$. The dynamic focusing at focal points $P_i$ includes adjusting a respective delay profile ($T_{ki}$) comprising a number of receive delays $T_{ki}$, to compensate for refraction of the ultrasonic transmission beam at the interface 22 between the component 10 and the standoff 18. These adjustments are performed as described above. In addition to dynamically focusing for each of the time intervals $t_i$, for the inspection method of this particular embodiment, the dynamic aperturing is performed for each time interval $t_i$. More particularly, the number of active receive elements is adjusted for each of the successive excitation time intervals $t_1$, as a function of the range $R_i$, to compensate for refraction of the ultrasonic transmission beam at the interface 22 between the component 10 and the standoff 18. To generate a focused echo signal for each range $R_i$, the delayed echo signals from all of the active receive elements are summed, for example in receiver 30, for each of the successive excitation time intervals.

Figure 5:
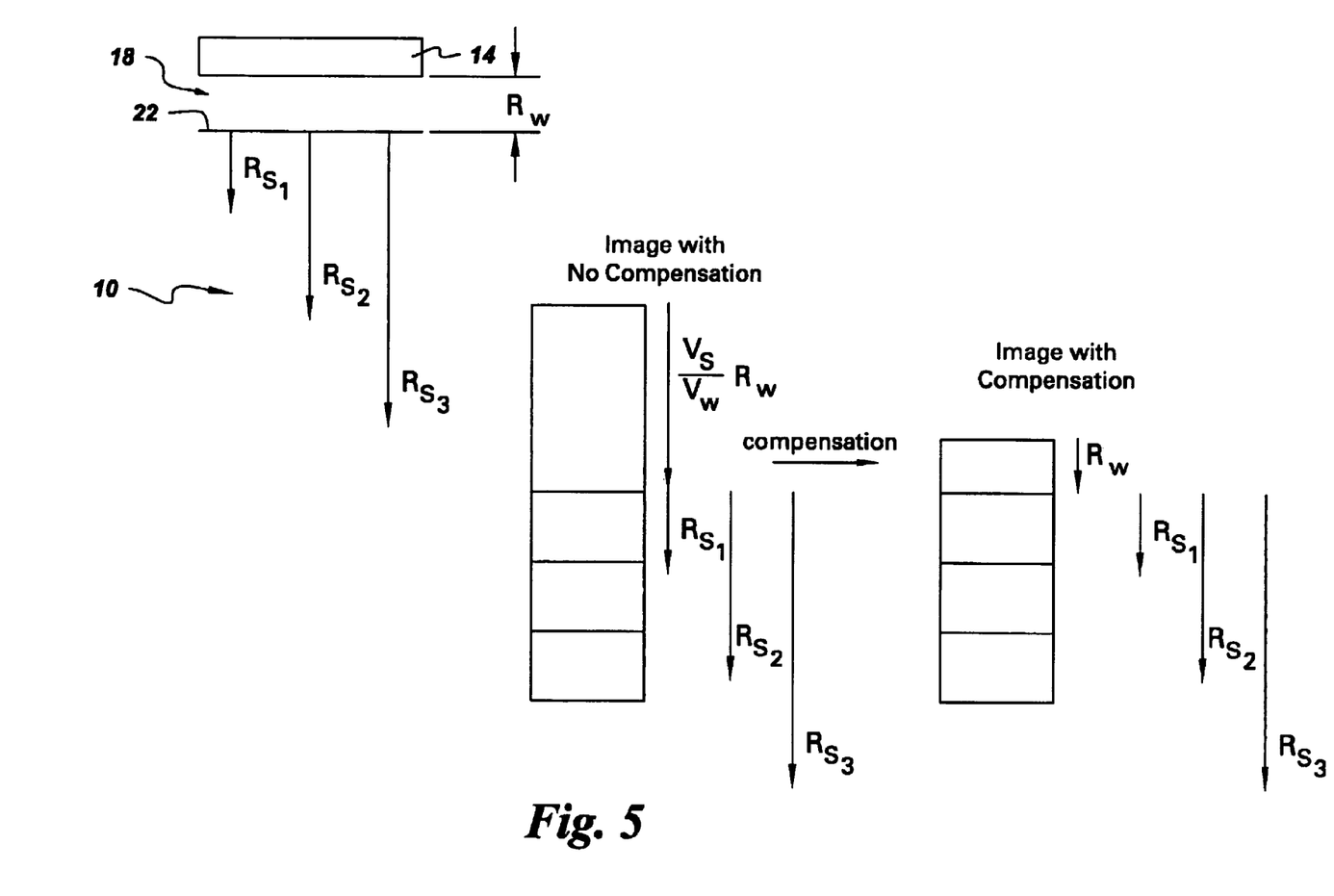
FIG. 5 shows a "stitched" image of a component with and without compensation for a standoff with a material velocity that differs from that of the component.

To display the resulting image data, it is useful to assemble (stitch) the image data from multiple depths into a single frame (image). This single frame is displayed using display system 17. Image stitching is known in the art and hence will not be described in detail here. However, it should be noted that when the imaging is done through a standoff 18, a conventional medical ultrasonic imaging system will distort the image due to the material velocity difference between the standoff 18 ($v_w$) and the component 10 ($v_s$). This distortion is shown in FIG. 5. As shown, the uncompensated image distorts the portion of the image corresponding to the standoff 18 by the ratio $v_s/v_w$. To compensate for the material velocity mismatch across the interface 22, the portion of the image corresponding to the standoff 18 is reduced by the ratio $v_s/v_w$, according to a particular embodiment. The compensated image is also shown in FIG. 5. Another correction is to remove the portion of the image corresponding to the standoff 18. Either of these corrections may be performed, for example, using the imaging software applied to display system 17.

B. Steering

Another method embodiment of the present invention is also described with reference to FIGS. 1 and 2. The method of inspecting a component 10 includes applying a separate excitation pulse to each transducer 12 forming array 14, to produce an ultrasonic transmission beam focused into the component 10 along a selected ray path 16 from the array 14. As shown in FIG. 2, the array 14 is separated from the component 10 by a standoff 18 with a material velocity $c_w$. The method further includes steering the ultrasonic transmission beam along the selected ray path at an angle θ relative to the surface normal 21. The steering includes adjusting a transmit delay profile ($T_k$) to compensate for refraction of the ultrasonic transmission beam at interface 22, as discussed above. The steering further includes modulating the excitation pulses with the transmit delay profile ($T_k$), as discussed above. The inspection method further includes generating a number of echo signals using the transducers 12 as receive elements 12, and processing the echo signals in a number of channels 20 using a delay profile. The delay profile comprises a set of receive delays, and each receive delay has a static receive steering term, as discussed above. The processing includes adjusting each of the static receive steering terms to compensate for refraction of the ultrasonic transmission beam at the interface 22 between the component 10 and the standoff 18, applying the delay profile ($T_k$) to the echo signals in the respective channels 20 to generate a number of delayed echo signals, and summing the delayed echo signals from the receive elements 12 to generate a steered echo signal. As discussed above with respect to the first embodiment, the echo signals are generated by each of the transducers 12 and applied separately to a receiver 30 through a set of switches 32. Each of the receive delays $T_k(\theta)$ is applied to the echo signal of the respective kth transducer 12 to form the respective delayed echo signal. The delayed echo signals are summed in the receiver 30.

In addition to steering the ultrasonic beam, it is useful to provide dynamic aperture sizing for inspection of industrial components. Accordingly, for a more particular embodiment the processing step further includes adjusting the number of active receive elements 12 as a function of a range R to provide a dynamic aperture 24 on receive. As noted above, an active receive element 12 is a transducer 12 from which the echo receive signal is included in the overall steered echo signal. In contrast, the echo signals from inactive receive elements 12 are neglected when calculating the steered echo signal. Because of the material velocity mismatch across interface 22, the adjustment of the number of receive elements 12 includes compensating for refraction of the ultrasonic transmission beam at the interface 22. For example, adjustment of the aperture width A is performed according to the expression: $F=[R_w+Rs(v_s/v_w)]/A$, as discussed above. As noted above, $R_w$ is the length of the beam extending along the central beam axis 16 in the standoff 18, $c_w$ is the material velocity in the standoff 18, $R_s$ is the length of the beam extending along the central beam axis 16 in the component 10, and $v_s$ is the material velocity in the component 10. $R_w$ and $R_s$ are exemplarily indicated in FIG. 2. For this steering plus dynamic aperture embodiment, the summing step comprises summing the delayed echo signals from all of the active receive elements 12 to generate the steered echo signal.

Although only one angle (θ) is indicated, those skilled in the art will recognize that the ultrasonic beam may also be steered with respect to multiple angles (θ, ψ). This embodiment encompasses both single-angle (θ) and multi-angle (θ, ψ) steering.

In addition to steering longitudinal waves, it would also be desirable to inspect industrial components by steering other wave modes. Industrial components 10, such as forgings, billets, welds (weldments) and other solids, support shear and surface wave propagation. Briefly, acoustic waves have three main propagation modes, longitudinal, shear and surface waves. Additional propagation modes include Lamb waves, Stonely waves, and extensional waves. The velocity of the shear wave $V_{sh}$ is about one half that of the longitudinal wave $v_L$ ($v_{sh} \sim 0.5\ v_L$), and the velocity of the surface wave $v_{su}$ is about 0.9 times that of the shear wave ($v_{su} \sim 0.9\ v_{sh}$). As discussed above with respect to FIG. 2, an ultrasonic beam incident on a standoff 18/component 10 interface 22 (for example a water/steel interface 22) at an angle θ is refracted in the component at a refracted angle θ, and the relationship between the incident and refracted angles is governed by Snell's Law: $\sin\theta/\sin\phi = v_w/v_s$. More particularly, each of the three modes has a distinct refracted angle φ. Namely, the longitudinal wave is refracted at an angle $\phi_L$, which is governed by $\sin\theta/\sin\phi_L = v_w/v_L$, the shear wave is refracted at an angle $\phi_{sh}$, which is determined by: $\sin\theta/\sin\phi_{sh} = v_w/v_{sh}$, and the surface wave is refracted at an angle $\phi_{su}$, which is determined by $\sin\theta/\sin\phi_{su} = v_w/v_{su}$. As the angle of incidence θ increases, the refracted angles $\phi_L$ and $\phi_{sh}$ increase until the respective critical angles $\phi_L = 90°$ and $\phi_{sh} = 90°$ are reached, at which point the respective longitudinal and shear modes no longer propagate in the component 10. The corresponding critical values of the incident angle θ are determined by Snell's Law and vary for the longitudinal and shear modes, due to the different velocities of the two modes $v_L$ and $v_{sh}$.

As noted above, industrial components 10 support shear and surface wave propagation. Accordingly, for another particular embodiment of the inspection method, a separate excitation pulse is applied to each of the transducers 12 to produce a shear wave ultrasonic transmission beam focused into the component 10. Beneficially, a shear wave has a wavelength $\lambda_{sh}$ equal to about half the wavelength $\lambda_L$ of a longitudinal wave at the same frequency, permitting greater resolution of defects. Moreover, if the incident angle θ exceeds the first critical angle $\phi_L$, the longitudinal wave does not propagate in the component 10 and use of the shear wave permits inspection of the component at the desired angle θ without erroneous longitudinal wave signals interfering with the ultrasonic inspection. Similarly, for another particular embodiment of the inspection method, a separate excitation pulse is applied to each of the transducers 12 to produce a surface wave ultrasonic transmission beam along the surface 22 of the component. Beneficially, ultrasonic inspection of industrial components using surface waves facilitates inspection of the surface 22 of the component, including detection of flaws located on the surface 22 of the component 10 (surface flaws). Conventional ultrasonic inspection employs longitudinal waves and hence is a volume inspection tool. Surface wave modes enhance surface flaw detection and inspection capabilities.

It will be recognized by those skilled in the art that the other inspection techniques described herein are also advantageously combined with these shear and surface wave mode inspections.

C. Surface Geometry

Figure 3:
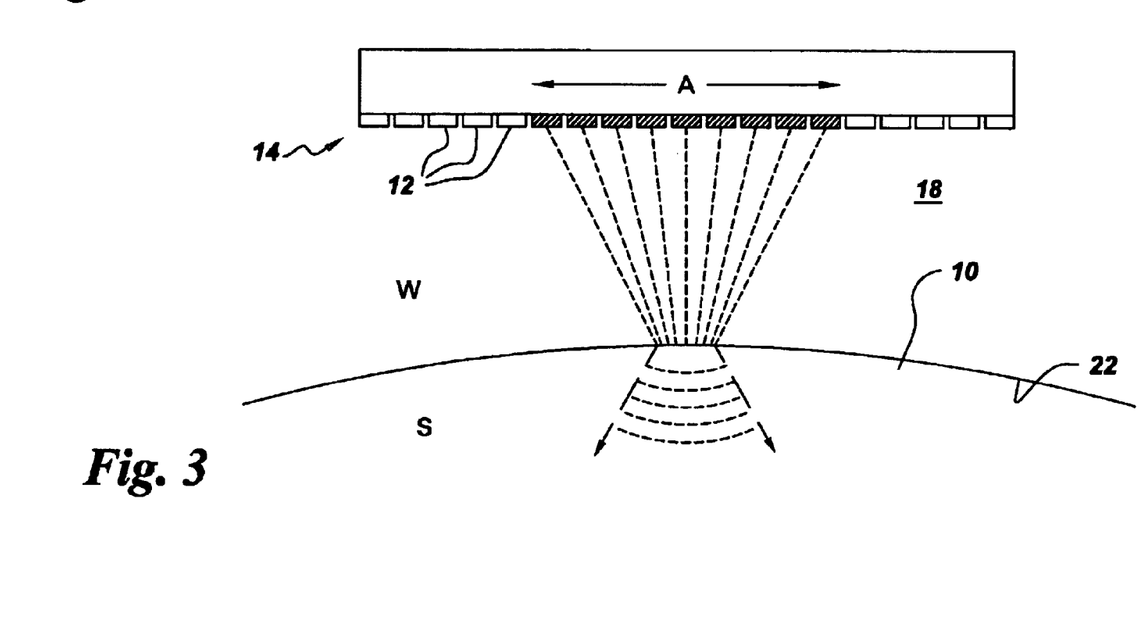
FIG. 3 shows a secondary lens effect cause by a standoff between an array of transducers and a component having a curved surface.

A method of inspecting a component 10 along a curved surface 22 of the component 10, for example, a conical, cylindrical or compound radii surface 22, and across a standoff 18 with a material velocity $c_w$ is described with reference to FIGS. 1 and 3. Because of the mismatch of material velocities $v_w$ in the standoff 18 and $v_s$ in the component 10, a curved interface 22 produces a secondary lens effect via refraction, with the standoff 18 functioning like a lens, changing the characteristics of the ultrasonic beam. This secondary lens effect is illustrated in FIG. 3 and degrades the resulting image. This inspection method embodiment corrects for the secondary lens effect and includes adjusting a transmit delay profile to compensate for at least one surface geometry effect. The transmit delay profile comprises a set of transmit delays $T_k$, and each of the transmit delays has a static surface geometry term, which is determined using Fermat's equations to calculate the delay required to have energy from each element 12 arrive at a desired focal point P in phase. The method further includes modulating a number of excitation signal pulses with the transmit delay profile ($T_k$). More particularly, the transmitter 28 imparts each of the transmit delays $T_k$ to the respective kth excitation signal pulse from one end of the array 14 (k=1) to the other end (k=N). The method further includes applying a separate one of each of the modulated excitation signal pulses to each of the transducers 12 forming array 14. The array 14 is separated a distance $R_w$ from the component 10. In this manner, an ultrasonic transmission beam is produced that is focused into the component 10 along a selected ray path 16 from the array 14. Via the static surface geometry term, application of the transmit delays $T_k$ corrects for the secondary lens effect upon transmit. The inspection method further includes generating a number of echo signals using the transducers 12 as receive elements 12 and processing the echo signals in a number of channels 20.

In addition to correcting for the secondary lens effect upon transmit, the inspection method also corrects for the secondary lens effect on receive. Accordingly, the processing of the echo signal includes applying a delay profile to the echo signals in the respective channels 20 to generate a number of delayed echo signals that compensate for the at least one surface geometry effect. Similar to the transmit delay profile, the delay profile comprises a set of receive delays ($T_k$), and each of the receive delays includes a static surface geometry term, which is also determined using Fermat's equations to calculate the delay required to have energy from each element 12 arrive at a desired focal point P in phase. More particularly, the static surface geometry terms are the same for both transmission and reception. More particularly, the receive delays $T_k$ are applied to the echo signals from the respective kth receive elements 12 by receiver 30 under the control of digital controller 19.

The processing of the echo signals further includes summing the delayed echo signals from the receive elements 12 to generate a surface geometry effect compensated echo signal. The echo signals are summed, for example, in receiver 30 under the control of digital controller 19.

D. Single Turn Inspection

Figure 4:
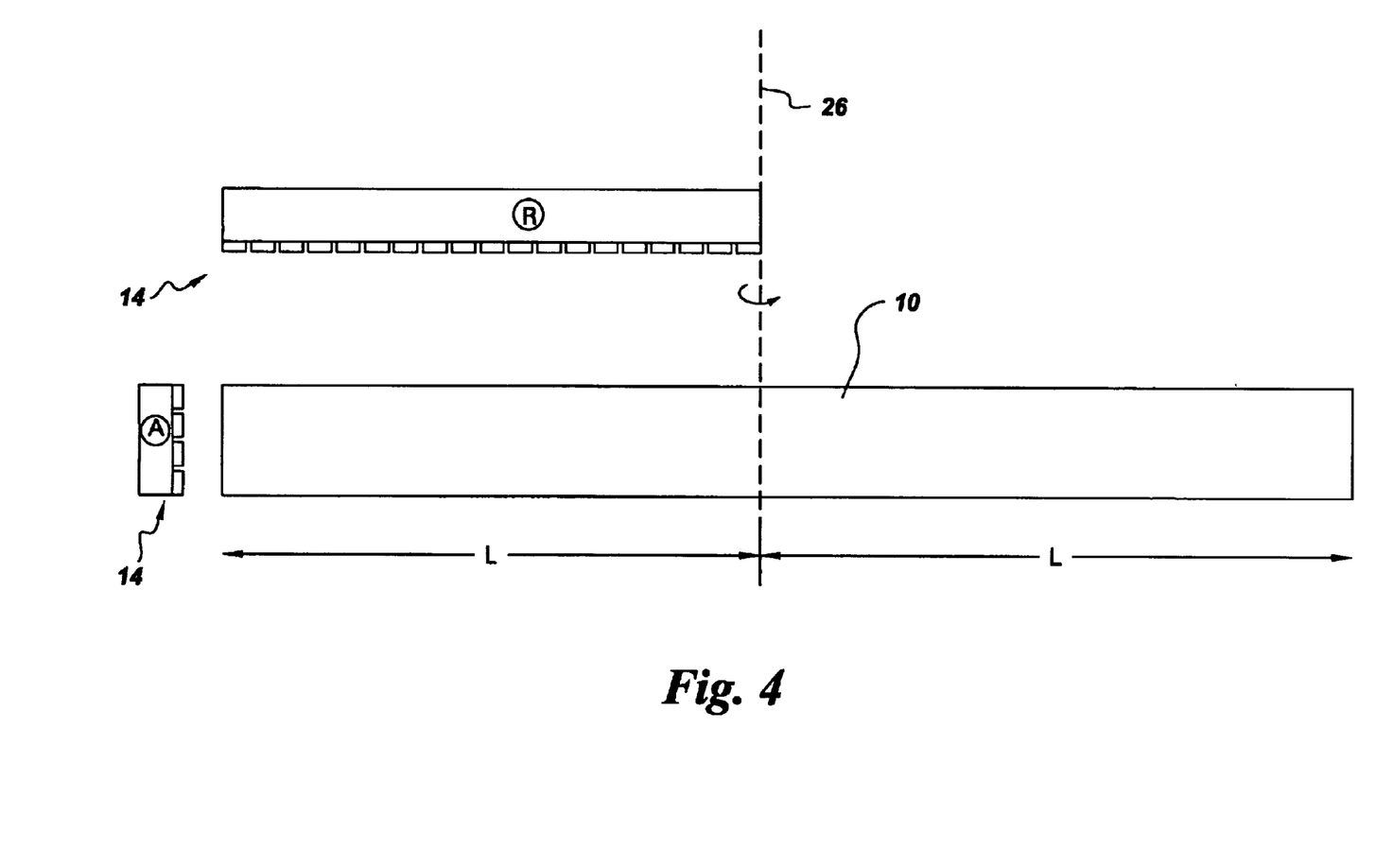
FIG. 4 illustrates a single-turn inspection method.

Industrial applications typically involve inspection of numerous components 10, such as billets and forgings. Accordingly, an efficient inspection process is critical to reducing inspection time and costs. In order to enhance inspection efficiency, a single-turn method embodiment is provided, for inspecting a component 10 having an inspection surface 22. The single-turn inspection method is described with reference to FIG. 4 and includes positioning an array 14 of transducers 12 facing the inspection surface 22 of the component 10, as shown for example in FIG. 4. The array 14 may face the inspection surface 22 either directly or across a standoff 18. In addition, the array 14 may be radially or axially aligned with the component 10. In FIG. 4, the arrays 14 marked "R" and "A" are respectively radially and axially aligned with the component 10. In addition, an array 14 may also be formed to extend both radially and axially along the component 10, for example arranged in a right angle (not shown). The single-turn inspection method further includes exciting the transducers 12 to produce an ultrasonic transmission beam focused into the component 10 along a selected ray path 16 from the array 14. A number of echo signals are generated using the transducers 12 as receive elements 12. The single-turn inspection method further includes changing the relative angular orientation of the array and the component around an axis 26 and repeating the steps of exciting the transducers 12 and generating a number of echo signals. The relative angular orientation of the array 14 and component 10 is changed either by rotating the array 14 or by rotating the component 10 around the axis 26. The echo signals are processed in a number of channels 20 to form at least one processed echo signal. Although the processing step is listed here as following the rotation of the array 14 around the axis 26, it should be understood that this order encompasses both sequential and collective processing. For sequential processing, the array 14 is satisfactorily positioned, the transducers 12 are activated, a set of echo signals is generated and processed. The array 14 is then rotated and the activation, generation and processing steps are repeated for a second set of echo signals, etc. Similarly, for collective processing, several sets of echo signals are generated for each angular increment of the array 14 about axis 26, and the sets of echo signals are then processed. The resulting processed echo signals are displayed, either as separate frames, or stitched together to form a single image of the components.

Beneficially, by inspecting the component 10 at a number of angular increments about the axis 26, translational movement of the array 14 across the component surface 22 can be avoided, increasing the overall efficiency of the inspection process. According to a particular embodiment of the single-turn method, the processed echo signals corresponding to a final image of the component 10 are obtained with the relative orientation of the array 14 and the component 10 constrained to rotations around the axis 26. By "constrained," it is meant that the final image is obtained at one or more rotational orientations of the array 14 (or component 10) around the axis 26, with no other repositioning of the array 14 relative to the component 10. For example, no translational movement of the array 14 relative to the components 10 is necessary for this embodiment. Desirably, for this embodiment, the array 14 is large enough to extend over the area of interest of the component 14, such that the entire area of interested is scanned by rotating the array 14 around the axis 26. For example, either a single large array or several smaller arrays grouped together are used. Beneficially, this embodiment avoids time-consuming and cumbersome repositioning of either the array 14 or the component 10.

According to a more particular embodiment applicable to components 10 with a curved inspection surface 22 (not shown in FIG. 4), the positioning step further includes contouring the array 14 to the curved inspection surface 22, either directly or through a standoff 18.

E. Through Transmission

Figure 6:
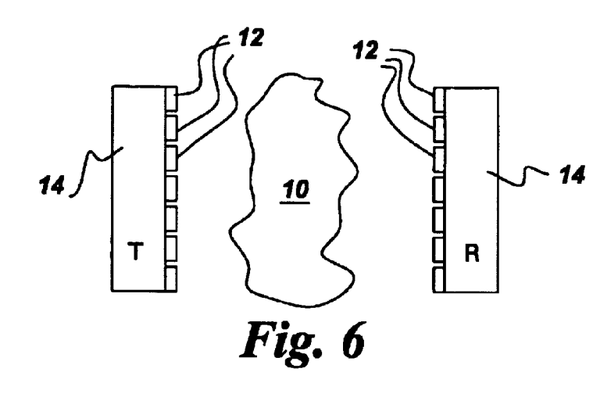
FIG. 6 illustrates a through-transmission inspection method.

In addition to single-array inspection, a component 10 may also be inspected by positioning the component 10 between a transmit array 14 and a receive array 14, as illustrated in FIG. 6. Conventionally, single ultrasound probes (not shown) are used to inspect a component 10 via through transmission ultrasound inspection. These probes are moved several times to scan the component. Beneficially, using arrays 14 for transmission and reception facilitates scanning the component 10 electronically, thereby eliminating time-consuming mechanical movement of the inspection equipment over the component 10

F. Pitch and Catch

Figure 7:
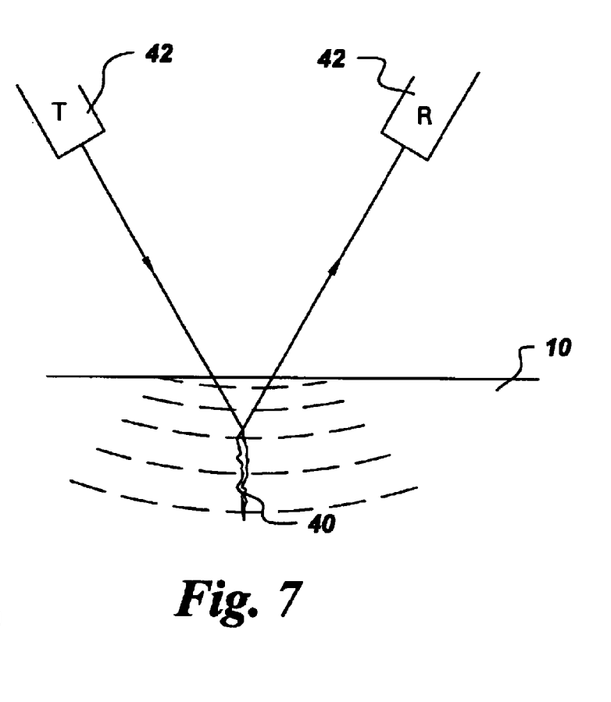
FIG. 7 illustrates a conventional "pitch and catch" inspection technique.
Figure 8:
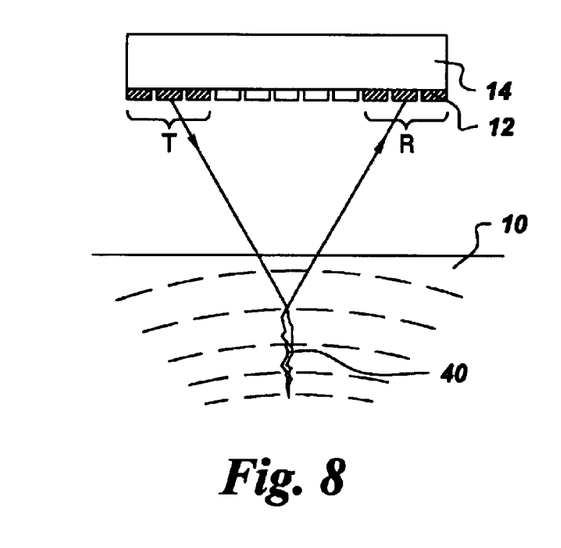
FIG. 8 shows an improved pitch and catch inspection technique using an array of transducers for both pitching and catching.
Figure 11:
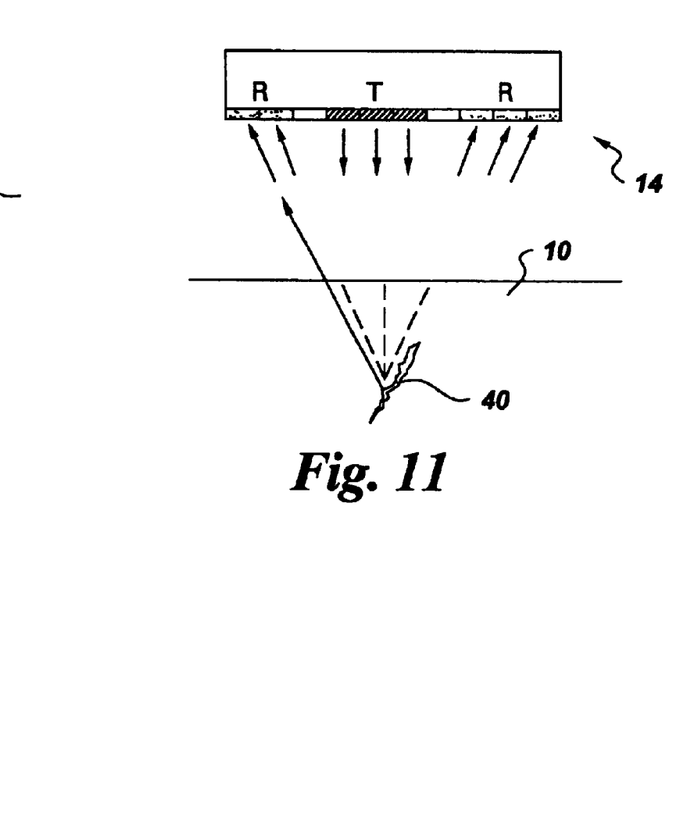
FIG. 11 illustrates another improved pitch and catch inspection technique using a single array of transducers for both pitching and catching.

Another conventional inspection technique is illustrated in FIG. 7. As shown, an ultrasound transmission beam is "pitched" into an inspection component 10 by a first probe 42 and "caught" by a second probe 42. This technique is employed for crack-tip diffraction detection. The configuration shown is used to detect the base and tip of a crack 40 in component 10 and, from this information, to size the crack 40. However, this technique requires mechanical manipulation of the probes 42 and hence is relatively slow and cumbersome. Replacing the individual probes 42 with arrays 14 of transducers 12 improves upon the technique described with reference to FIG. 7. FIGS. 8 and 11 illustrate an improved "pitch and catch" inspection method for which a single array 14 is used for both pitching and catching. More particularly, at least one subset of the transducers 12 in the array 14 is energized for transmission of the ultrasonic beam, and at least one subset of the transducers 12 receives the reflected ultrasonic energy. The respective transmit and receive subsets of transducers 12 are indicated in FIGS. 8 and 11 by "T" and "R." As shown in FIG. 8, one subset of transducers 12 may be used on transmit, and one subset may be used on receive. For the embodiment of FIG. 11, one subset of transducers 12 is used on transmit, whereas two subsets are used on receive. This single-array pitch and catch embodiment is not limited to the specific configurations illustrated in FIGS. 8 and 11 but rather encompasses any arrangement of a single array 14 for which at least one set of transducers form a beam on transmission and at least one other set of transducers 12 receive a reflected beam from the test component 10.

G. Doppler

It is known to use ultrasound to measure blood flow and would be desirable to extend ultrasound techniques developed to monitor blood flow to industrial applications, such as monitoring product flow through tubing or pipes (for example chemical feed pipes) or through instrumentation pipes (used, for example, for heat exchanger flow). Pipes, tubing, and other vessels through which products flow in industrial applications are collectively termed "pipes" herein. Inspection of product flow through pipes is desirable because deposits (or build-up) on pipe walls can restrict and/or perturb product flow through the pipes. In addition, heat exchangers can plug or foul causing flow restrictions. Ultrasound desirably provides a nondestructive, noninvasive inspection method for detecting and monitoring such problems.

Figure 9:
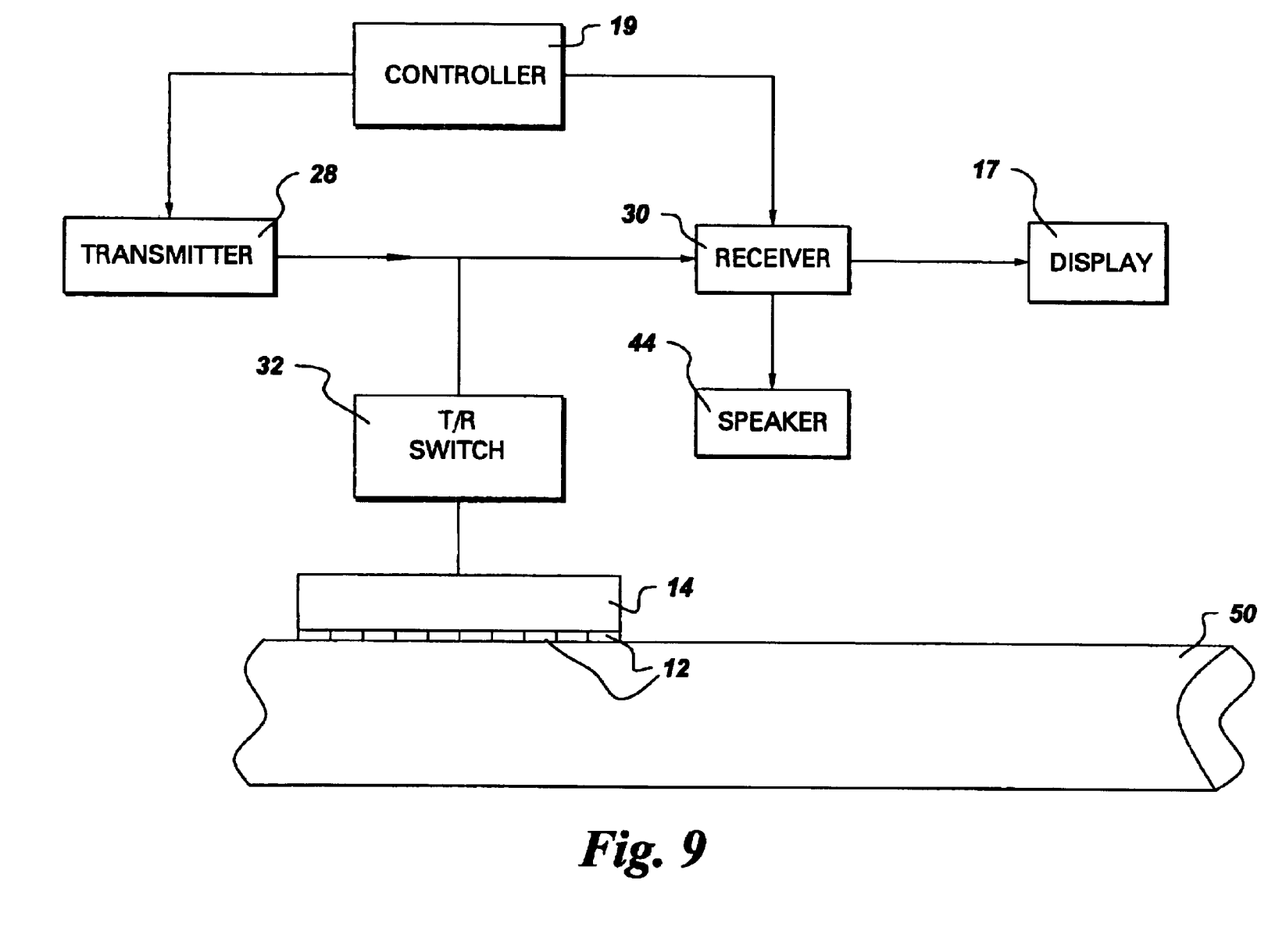
FIG. 9 illustrates a method of inspecting product flow through a pipe.

A method of inspecting product flow through a pipe 50 is described with reference to FIG. 9. The method includes exciting a number of transducers 12 forming an array 14 to transmit ultrasonic energy into the pipe 50. For example, the transducers 12 are excited by transmitter 28 through T/R (transmit/receive) switches 32 under control of controller 19. It should be noted that although the array 14 is depicted in FIG. 9 as being in contact with the pipe 50, the array 14 and pipe 50 may also be separated by a standoff, for example by water, another liquid suitable for coupling the ultrasonic energy to the pipe 50 and array 14, or a shoe (not shown). The method further includes generating a number of receive signals from reflected ultrasonic energy and processing the receive signals in a number of channels 20. The receive signals are generated by the transducers 12 acting as receive elements 12, for the embodiment shown in FIG. 9. The processing includes comparing the receive signals to a frequency reference to determine a number of frequency shifts imparted to the reflected ultrasonic energy. The processing is performed, for example, by receiver 30 which is controlled by digital controller 19. According to a more particular embodiment, the processing further includes producing an image of the product flow through the pipe 50. For the embodiment of FIG. 9, the image is displayed on display 17 using known imaging software (not shown). By imaging the product flow through the pipe, flow restrictions caused by deposits on pipe walls can be detected and monitored.

For another embodiment, the inspection method further includes converting the frequency shifts to an audible output. For example, the frequency shifts are converted to an audible output, which is transmitted over at least one speaker 44, using known audio software (not shown) such as provided in the GE LOGIQ 9. Converting the frequency shifts to an audible output, provides a quick means for detection by an operator of a problem with the product flow through the pipe.

H. Full Array Insonification

Figure 10:
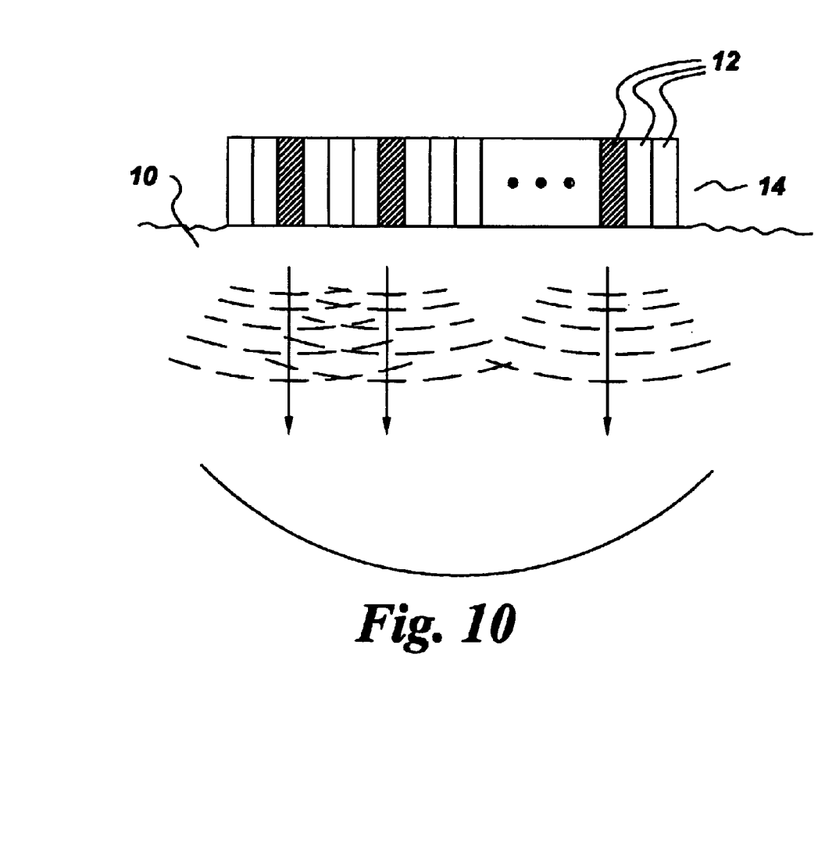
FIG. 10 illustrates the simultaneous excitation of each of a first set of transducers in an array.

To enhance the signal-to-noise ratio for ultrasonic inspection of industrial components, another industrial ultrasonic inspection method incorporates full array insonification. This method of inspecting a component 10 is described with reference to FIG. 10. The inspection method includes simultaneously exciting a first set of transducers 12 in an array 14, as exemplarily shown in FIG. 10. The exemplary first set of transducers 12 is indicated by the shaded transducers 12. The signal-to-noise ratio increases with the number of transducers 12 included in this first set. According to a particular embodiment, the first set of transducers 12 includes all of the transducers forming the array 14. In other words, for this particular embodiment, each of the transducers 12 forming the array 14 is excited simultaneously, thereby providing full array insonification. The first set of transducers is excited, for example, by transmitter 28, under the control of digital controller 19.

The inspection method further includes receiving a set of backscattered ultrasound signals from the component 10 using a second set of transducers 12 in the array as receive elements 12 and generating a plurality of receive signals from the backscattered ultrasound signals using the receive elements 12. According to a particular embodiment, the second set of transducers 12 includes all of the transducers 12 forming the array 14. The method further includes processing the receive signals to form a set of beam form image data. The receive signals are processed, for example by receiver 30, under the control of digital controller 19. These processing steps are known, and exemplary processing steps are described in commonly assigned U.S. Pat. No. 6,048,315, Chiao et al., entitled "Method and Apparatus for Ultrasonic Synthetic transmit Aperture Imaging Using Orthogonal Complementary Codes," which is incorporated by reference herein.

By simultaneously exciting a first set of the transducers 12, an entire region of interest within the component 10 is insonified, eliminating a need to electronically scan the component 10 via the consecutive excitation of the transducers 12 forming the array 14. In this manner, the method illustrated in FIG. 10 increases the speed at which inspection data can be obtained, relative to consecutive driving of the transducers 12 forming an inspection array 14. The corresponding reduction in imaging (and hence inspection) time enhances productivity, which is particularly beneficial in industrial settings. Application of this method embodiment to inspect billets is beneficial, in that a billet 10 is fully insonified by driving the first set of transducers 12 once, reducing the inspection time relative to consecutive firing of the transducers 12.

I. Image Location

Ultrasound inspection systems for medical applications are advanced and provide a number of desirable features for industrial applications, such as dynamic focusing, dynamic aperture, steering, and Doppler frequency shifts. Examples of advanced ultrasonic inspection systems used for medical applications include the GE LOGIQ 9 and the GE LOGIQ Book. However, ultrasonic inspection systems used for medical applications typically employ a predefined scan rate based on an arbitrary timing reference, which triggers a new image forming sequence. By "arbitrary," it is meant that the timing reference is not linked to position of the array. However, for industrial applications, it is desirable to identify the position at which a given frame (image) was acquired, in order to fully characterize the component 10 after inspection. Accordingly, the inspection methods described above preferably acquire an image (frame) synchronous to the relative position between the array 14 and the component being inspected. More particularly, the timing reference employed is selected for synchronization with the relative position of the array 14 and component 10. For example, encoders may be used to track the position of an axis of motion. A common pulse/position synchronization technique is termed "pulse on position" (or "POP") and applies a TTL level pulse when a mechanical system (here the array 14) arrives at the next data acquisition position.

As noted above, many ultrasonic inspection systems used for medical applications, such as the GE LOGIQ 9 and the GE LOGIQ Book, typically do not synchronize an image with the position at which it is acquired. Accordingly, for another embodiment of the invention, ultrasonic inspection systems, such as the GE LOGIQ 9 and the GE LOGIQ Book, are modified to acquire data synchronous to the mechanical position of the array 14. More particularly, the timing inputs and outputs are adapted to correlate with position. Exemplary timing inputs to ultrasonic inspection systems used for medical applications include the circuitry for EKG inputs or for foot pedal switches (not shown).

Although only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method of inspecting a component comprising:
  (a) exciting a plurality of transducers forming an array to produce an ultrasonic transmission beam focused into the component along a selected ray path from the array, the array being separated from the component by a standoff with a material velocity
  (b) generating a plurality of echo signals using the transducers as receive elements; and
  (c) processing the echo signals in a plurality of channels, said processing comprising:
    (i) dynamically focusing the echo signals along the selected ray path on at least one focal point P in the component, wherein said dynamic focusing comprises:
    adjusting a delay profile to compensate for refraction of the ultrasonic transmission beam at an interface between the component and the standoff; and
    applying the delay profile to the echo signals in the respective channels to generate a plurality of delayed echo signals;
    (ii) adjusting the number of active receive elements as a function of a range $R_s$ to provide a dynamic aperture on receive, wherein said adjustment of the number of receive elements comprises compensating for refraction of the ultrasonic transmission beam at the interface between the component and the standoff; and
    (iii) summing the delayed echo signals from all of the active receive elements to generate a focused echo signal.

2. The inspection method of claim 1, wherein said excitement of the transducers comprises applying a separate excitation signal pulse to each of the transducers, said inspection method further comprising:
  (d) steering the ultrasonic transmission beam along the selected ray path at an angle θ relative to a surface normal, said steering comprising:
    (i) adjusting a transmit delay profile to compensate for refraction of the ultrasonic transmission beam at the interface between the component and the standoff, the transmit delay profile comprising a plurality of transmit delays, with each transmit delay comprising a static steering term, and
    (ii) modulating the excitation signal pulses with the transmit delay profile; and
  (e) forming a steered focused echo signal by said application of the delay profile to the echo signals in the respective channels to generate the delayed echo signals, wherein said delay profile comprises a plurality of receive delays, with each receive delay comprising a static receive steering term, and wherein said adjustment of the delay profile adjusts each of the static receive steering terms to compensate for refraction at the interface.

3. The inspection method of claim 2, wherein said steering comprises steering the ultrasonic transmission beam along the selected ray path at angles θ and ψ.

4. The inspection method of claim 1, wherein:

said excitement of the transducers comprises applying a separate signal pulse to each of the transducers at each of a plurality of successive excitation time intervals $t_i$, said generation of the echo signals is performed for each of the successive excitation time intervals $t_i$, said dynamic focusing comprises dynamically focusing the echo signals along the selected ray path on a plurality of focal points $P_i$ at various ranges $R_i$ during each successive i-th one of the excitation time intervals $t_i$, said adjustment of the number of active receive elements is performed for each of the successive excitation time intervals $t_i$ as a function of the range $R_i$, and said summation of the delayed echo signals from all of the active receive elements is performed for each of the successive excitation time interval to generate a focused echo signal for the respective range $R_i$.

5. A method of inspecting a component comprising:

(a) applying a separate excitation pulse to each of a plurality of transducers forming an array to produce an ultrasonic transmission beam focused into the component along a selected ray path from the array, the array being separated from the component by a standoff with a material velocity $v_w$;

(b) steering the ultrasonic transmission beam along the selected ray path at an angle θ relative to a surface normal, said steering comprising:

(i) adjusting a transmit delay profile to compensate for refraction of the ultrasonic transmission beam at the interface between the component and the standoff, the transmit delay profile comprising a plurality of transmit delays, each transmit delay comprising a static steering term, and (ii) modulating the excitation pulses with the transmit delay profile;

(c) generating a plurality of echo signals using the transducers as receive elements; and (d) processing the echo signals in a plurality of channels using a delay profile, the delay profile comprising a plurality of receive delays, each receive delay comprising a static receive steering term, said processing comprising:

(i) adjusting each of the static receive steering terms to compensate for refraction of the ultrasonic transmission beam at the interface between the component and the standoff;

(ii) applying the delay profile to the echo signals in the respective channels to generate a plurality of delayed echo signals; and (iii) summing the delayed echo signals from the receive elements to generate a steered echo signal.

6. The inspection method of claim 4, wherein said processing step further comprises:

(iv) adjusting the number of active receive elements as a function of a range $R_s$ to provide a dynamic aperture on receive, wherein said adjustment of the number of receive elements comprises compensating for refraction of the ultrasonic transmission beam at the interface between the component and the standoff, wherein said summing step comprises summing the delayed echo signals from all of the active receive elements to generate the steered echo signal.

7. The inspection method of claim 5, wherein said steering comprises steering the ultrasonic transmission beam along the selected ray path at angles θ and ψ.

8. The inspection method of claim 5, wherein said application step comprises applying a separate excitation pulse to each of the transducers to produce a sheer wave ultrasonic transmission beam focused into the component.

9. The inspection method of claim 5, wherein said application step comprises applying a separate excitation pulse to each of the transducers to produce a surface wave ultrasonic transmission beam focused along the surface of the component.

10. A method of inspecting a component along a curved surface of the component and across a standoff with a material velocity $v_w$, said inspection method comprising:

(a) adjusting a transmit delay profile to compensate for at least one surface geometry effect, the transmit delay profile comprising a plurality of transmit delays, each of the transmit delays comprising a static surface geometry term;

(b) modulating a plurality of excitation signal pulses with the transmit delay profile;

(c) applying the modulated excitation signal pulses to a plurality of transducers forming an array separated from the component by the standoff, to produce an ultrasonic transmission beam focused into the component along a selected ray path from the array;

(d) generating a plurality of echo signals using the transducers as receive elements; and (e) processing the echo signals in a plurality of channels, said processing comprising:

(i) applying a delay profile to the echo signals in the respective channels to generate a plurality of delayed echo signals that compensate for at least one surface geometry effect, the delay profile comprising a plurality of receive delays, each of the receive delays comprising a static surface geometry term; and (ii) summing the delayed echo signals from the receive elements to generate a surface geometry effect compensated echo signal.

11. A single-turn method of inspecting a component having an inspection surface, said single-turn inspection method comprising:

(a) positioning an array of transducers facing the inspection surface of the component;

(b) exciting the transducers to produce an ultrasonic transmission beam focused into the component along a selected ray path from the array;

(c) generating a plurality of echo signals using the transducers as receive elements;

(d) changing the relative angular orientation of the array and the component around an axis and repeating steps (b) and (c); and (e) processing the echo signals in a plurality of channels to form at least one processed echo signal, wherein the processed echo signals corresponding to a final image of the component are obtained with the relative orientation of the array and the component constrained to rotation around the axis.

12. The single-turn inspection method of claim 11, wherein the component has a curved inspection surface, and wherein said positioning step further comprises contouring the array to the curved inspection surface.

* * * * *